(12) United States Patent
Gonzalez et al.

(10) Patent No.: US 10,864,326 B2
(45) Date of Patent: Dec. 15, 2020

(54) MEDICATION INJECTION DEVICE WITH AUTOMATIC NEEDLE RETRACTION FOLLOWING INJECTION

(71) Applicant: Eli Lilly and Company, Indianapolis, IN (US)

(72) Inventors: Nicole Taylor Gonzalez, Indianapolis, IN (US); Gregory Alan Musselman, Hartford, CT (US); Lisa Jeanne Nelson, Minneapolis, MN (US); Daniel Enluo Wang, Richmond, VA (US)

(73) Assignee: Eli Lilly and Company, Indianapolis, IN (US)

( * ) Notice: Subject to any disclaimer, the term of this patent is extended or adjusted under 35 U.S.C. 154(b) by 135 days.

(21) Appl. No.: 16/079,414

(22) PCT Filed: Mar. 10, 2017

(86) PCT No.: PCT/US2017/021761
§ 371 (c)(1),
(2) Date: Aug. 23, 2018

(87) PCT Pub. No.: WO2017/160625
PCT Pub. Date: Sep. 21, 2017

(65) Prior Publication Data
US 2019/0009026 A1 Jan. 10, 2019

Related U.S. Application Data

(60) Provisional application No. 62/308,997, filed on Mar. 16, 2016.

(51) Int. Cl.
*A61M 5/178* (2006.01)
*A61M 5/20* (2006.01)
*A61M 5/32* (2006.01)

(52) U.S. Cl.
CPC .......... *A61M 5/2033* (2013.01); *A61M 5/326* (2013.01); *A61M 2005/206* (2013.01);
(Continued)

(58) Field of Classification Search
CPC .. A61M 5/2033; A61M 5/326; A61M 5/3234; A61M 5/158; A61M 5/322;
(Continued)

(56) References Cited

U.S. PATENT DOCUMENTS

2008/0188798 A1  8/2008  Weber
2010/0049125 A1*  2/2010  James ................ A61M 5/2033
                                                        604/110

(Continued)

FOREIGN PATENT DOCUMENTS

EP  20122489380  8/2012
EP  20132606924  6/2013
(Continued)

OTHER PUBLICATIONS

Patent Cooperation Treaty International Search Report and the Written Opinion of the International Searching Authority pertaining to International Application No. PCT/US2017/021776; dated May 30, 2017.
(Continued)

*Primary Examiner* — Nathan R Price
*Assistant Examiner* — Tania Ismail
(74) *Attorney, Agent, or Firm* — M. Daniel Spillman

(57) ABSTRACT

An automatic medication injection device including a driver (95), a retractor (190, 230) and a blocking member (180). Upon device triggering the driver is shifted proximally to
(Continued)

move a device syringe, expel medication from the syringe0, and then to disengage itself from the syringe plunger. The driver and the blocking member have a complementary camming configuration by which the blocking member, during the driver shifting, is automatically rotated from a first rotational orientation to a second rotational orientation. The blocking member blocks retraction of the retractor when disposed in the first rotational orientation, and permits retraction of the retractor when disposed in the second rotational orientation, which retractor retraction withdraws the device syringe from an injecting position to a retracted position.

20 Claims, 16 Drawing Sheets

(52) U.S. Cl.
CPC ............... *A61M 2005/2013* (2013.01); *A61M 2005/2073* (2013.01)

(58) Field of Classification Search
CPC .............. A61M 5/3232; A61M 5/3271; A61M 2005/2013; A61M 2005/206
See application file for complete search history.

(56) References Cited

U.S. PATENT DOCUMENTS

| | | |
|---|---|---|
| 2010/0185178 A1 | 7/2010 | Sharp et al. |
| 2012/0253314 A1 | 10/2012 | Harish et al. |

FOREIGN PATENT DOCUMENTS

| | | |
|---|---|---|
| WO | 03008023 | 1/2003 |
| WO | 2008112472 | 9/2008 |
| WO | 2009040602 | 4/2009 |
| WO | 2009040607 | 4/2009 |
| WO | 2009062508 | 5/2009 |
| WO | 2012000832 | 1/2012 |
| WO | 2012000835 | 1/2012 |
| WO | 2013034651 | 3/2013 |
| WO | 2014062488 | 4/2014 |
| WO | 2017160625 | 9/2017 |
| WO | 2017160626 | 9/2017 |

OTHER PUBLICATIONS

Patent Cooperation Treaty International Search Report and the Written Opinion of the International Searching Authority pertaining to International Application No. PCT/US2017/021761; dated Jun. 23, 2017.

\* cited by examiner

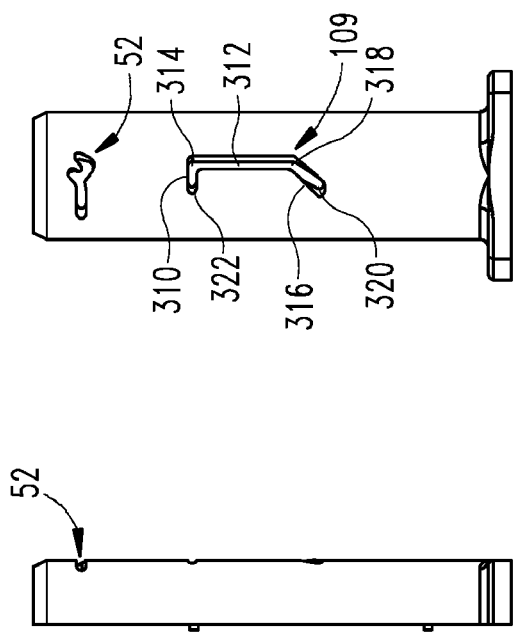
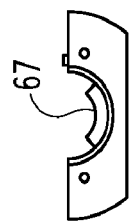
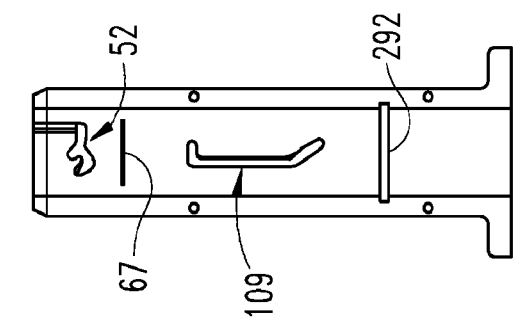
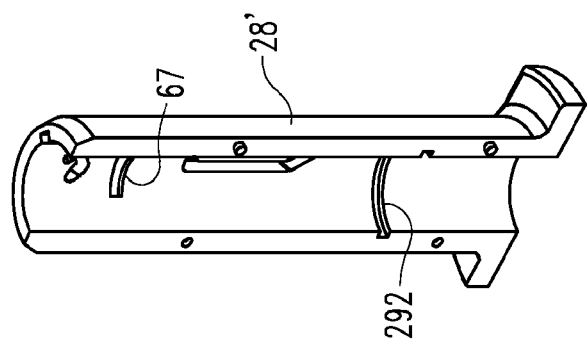
Fig. 4a  Fig. 4b  Fig. 4c  Fig. 4d  Fig. 4e  Fig. 4f

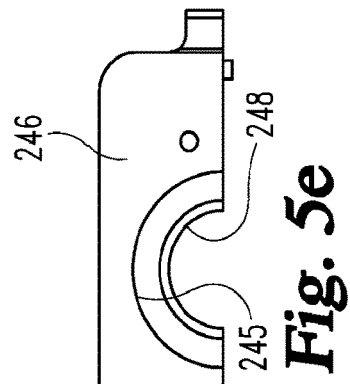
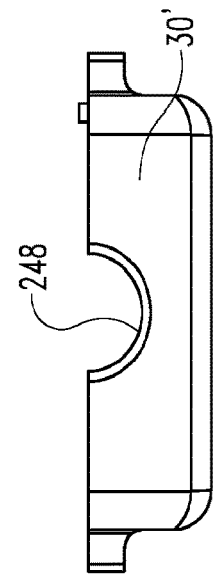
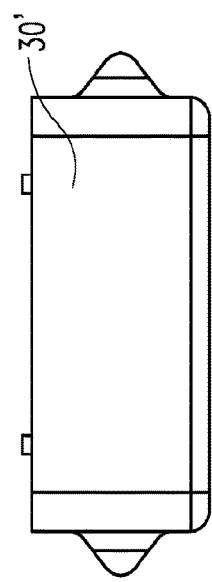
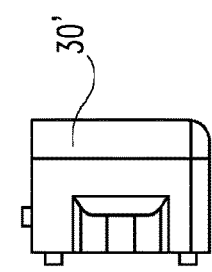
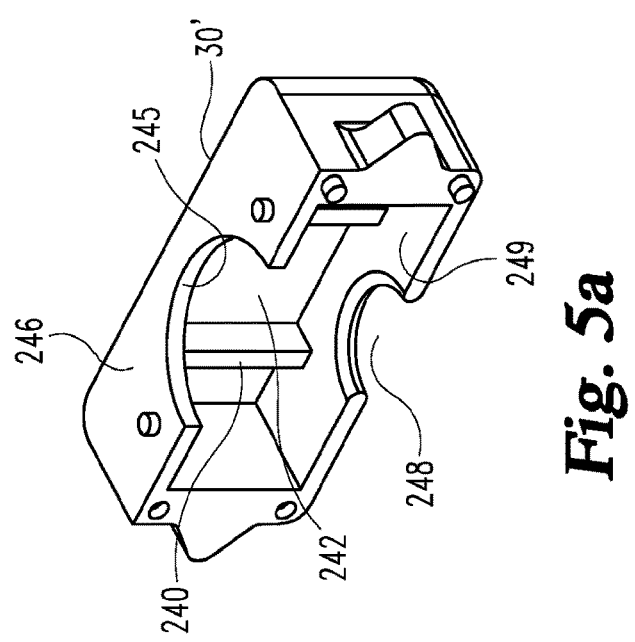
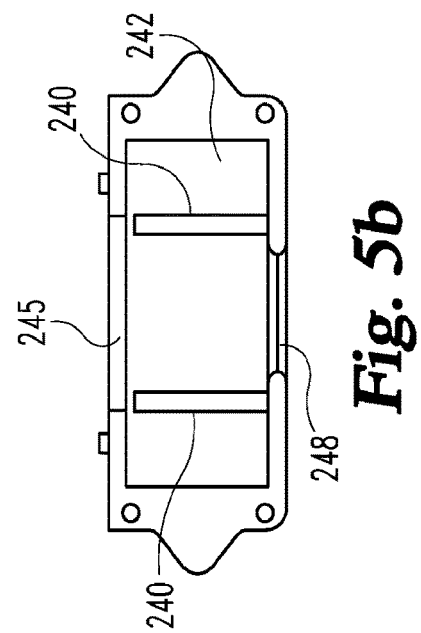

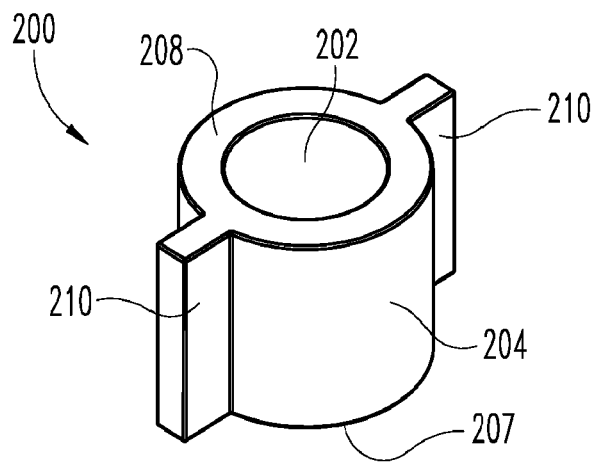
*Fig. 12a*
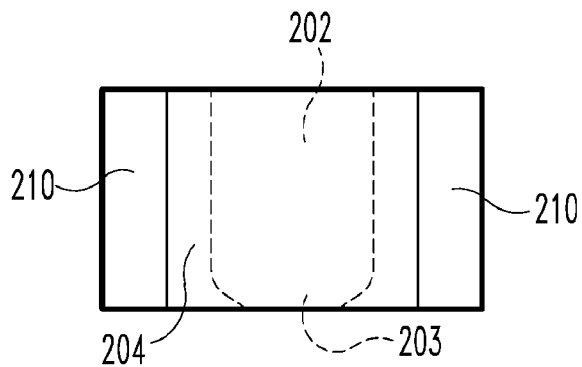 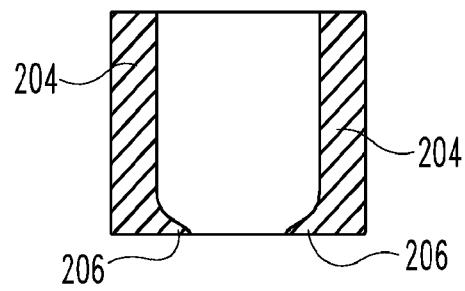
*Fig. 12b*  *Fig. 12c*
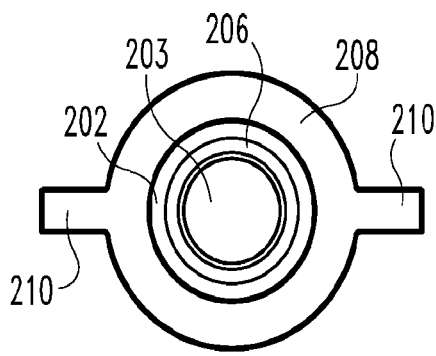 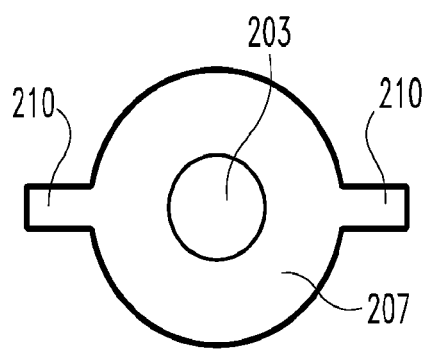
*Fig. 12d*  *Fig. 12e*

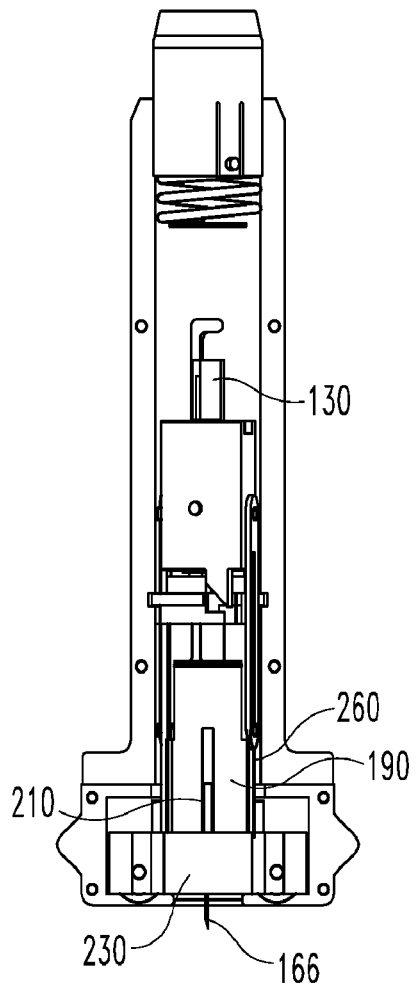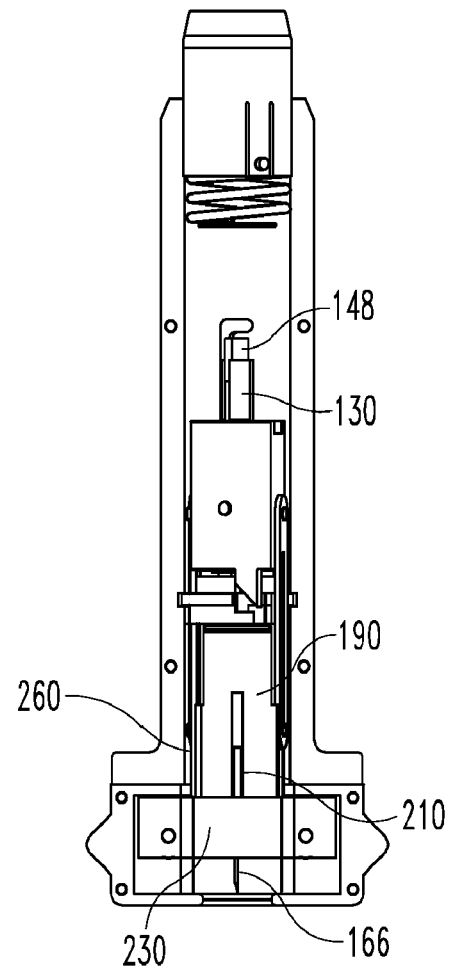
*Fig. 16*  *Fig. 17*

MEDICATION INJECTION DEVICE WITH AUTOMATIC NEEDLE RETRACTION FOLLOWING INJECTION

BACKGROUND OF THE INVENTION

The present invention pertains to pharmaceutical injection devices, and, in particular, to an automatic medication injection device that automatically retracts a needle after an injection.

Patients suffering from a number of different diseases frequently must inject themselves with pharmaceuticals. A variety of devices have been proposed to facilitate these injections. One type of device is an automatic medication injection device. This type of device typically includes a trigger assembly that when operated by a user causes the device to automatically insert into the user a needle of a syringe that prior to triggering was disposed within the device housing, and then the device automatically injects a dose of medication through that inserted needle.

While perhaps useful, some automatic medication injection devices do suffer from one or more shortcomings. For example, some known automatic medication injection devices require a user to pull the device away from an injection site in order to withdraw the needle from the skin after an injection. Such devices, whether the needle withdrawal be completely manual or be spring-powered when triggered by a user starting to pull the device away from an injection site, may be found undesirable to use by some people.

Some automatic medication injection devices may insert a needle or inject at speeds which have variability during the course of the device use which do not promote an appropriate experience for some users. In addition, some automatic medication injection devices are bulky so as to make the device less convenient to use inconspicuously.

Thus, it would be desirable to provide an automatic medication injection device that can overcome one or more of these and other shortcomings of the prior art.

BRIEF SUMMARY

In one form thereof, the present invention provides an automatic medication injection device including: a housing; a syringe filled with medication and including a needle and a plunger; a driver shiftable proximally in the housing along a track from a ready position to a plunged position, the driver and the track and the plunger being complementarily configured for the driver, when shifted from the ready position to the plunged position, to advance the plunger to move the syringe proximally from a start position, at which the needle is disposed within the housing, to an injecting position, at which the needle projects external to the housing, and to advance the plunger to expel medication from the syringe through the needle, and to disengage from the plunger to permit axial movement of the driver relative to the plunger; a retractor having an opening in which the syringe extends, the retractor shiftable distally within the housing from a ready position to a retraction position to withdraw the syringe from the injecting position to a retracted position at which the needle is disposed within the housing; a blocking member having an opening in which the syringe extends, the blocking member rotatable within the housing from a first rotational orientation to a second rotational orientation, the blocking member complementarily configured with the retractor to block movement of the retractor from the ready position to the retraction position when disposed in the first rotational orientation, and to permit movement of the retractor from the ready position to the retraction position when disposed in the second rotational orientation; at least one biasing member preloaded to urge the driver proximally and to urge the retraction member distally; a trigger actuatable to allow the at least one biasing member to move the driver from the ready position to the plunged position; and the driver and the blocking member having a complementary camming configuration for the blocking member to be forcibly rotated automatically from the first rotational orientation to the second rotational orientation when the driver shifts from the ready position to the plunged position.

One advantage of the present invention is that an automatic medication injection device may be provided which provides for needle insertion, injection, and then retraction during use in an automatic manner without user intervention after an initial device triggering.

Another advantage of the present invention is that an automatic medication injection device may be provided which is easy to handle and use.

Another advantage of the present invention is that an automatic medication injection device may be provided which can insert a needle and/or inject through a needle at one or more relatively constant speeds.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein:

FIGS. 4a, 4b, 4c, 4d, 4e and 4f are respectively perspective, front, back, side, top and bottom views of a shell half of the housing upper portion shown separate from the other device components;

FIGS. 5a, 5b, 5c, 5d, 5e and 5f are respectively perspective, front, back, side, top and bottom views of a shell half of the housing lower portion shown separate from the other device components;

FIGS. 12a, 12b, 12c, 12d and 12e are respectively perspective, side, front in longitudinal cross-section, top and bottom views of a syringe guide shown separate from the other device components;

FIG. 16 is a front view similar to the view of FIG. 2 after the medication in the device has been delivered and immediately prior to needle retraction; and FIG. 17 is a front view similar to the view of FIG. 16 after needle retraction.

Figure 1:
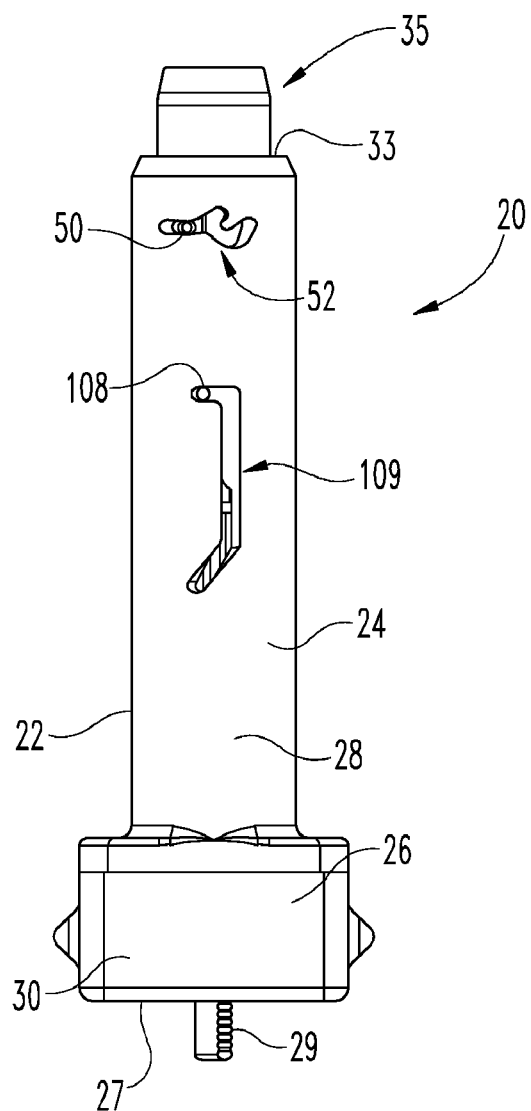
FIG. 1 is a front view of an automatic medication injection device, which device is shown in a locked arrangement prior to use.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION

Figure 2:
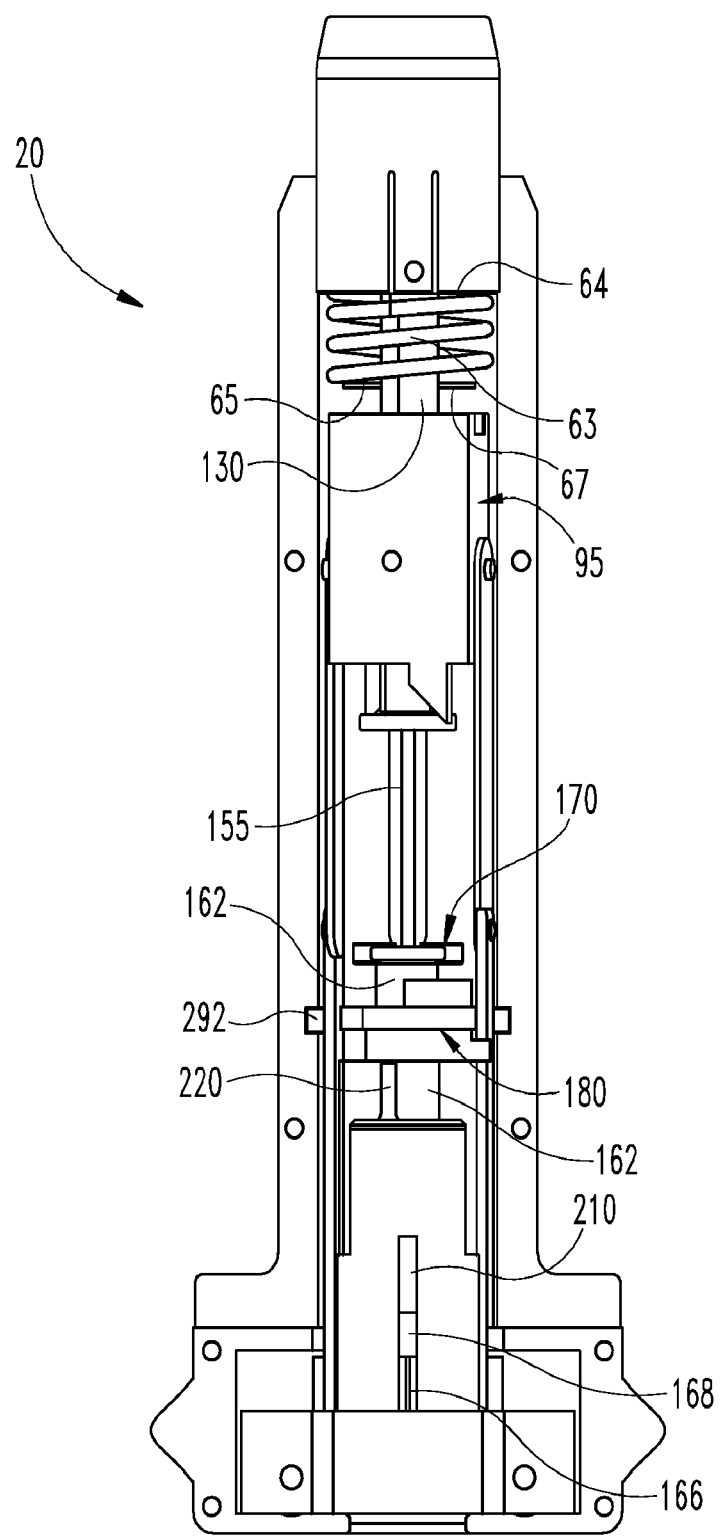
FIG. 2 is a front view of the automatic medication injection device of FIG. 1 with both the needle shield and the front half of the housing removed, and after the device has been shifted from the locked arrangement to an unlocked or ready arrangement.

Referring now to FIGS. 1 and 2, there are shown two views of an automatic medication injection device, generally designated 20. When the trigger assembly of device 20 is operated, the needled syringe of the device 20 is automatically driven downward such that its injection needle projects beyond the bottom end 27 of the device housing to penetrate the user. The device then proceeds to inject automatically, that is without further user action, the medication contents of the syringe through the needle, after which the syringe is retracted automatically such that the needle is returned to within the housing.

Device 20 includes an outer housing 22 in which are operationally disposed working components of the device. The outer housing 22 is formed by an upper portion 24 and a lower portion 26. The housing upper portion 24 is formed by two identical, mating shell halves 28, 28' that are fixedly secured together. The housing lower portion 26 is also formed by two identical, mating shell halves 30, 30' that are fixedly secured together. The housing upper portion 24 and housing lower portion 26 are also fixedly secured to each other. Suitable manners of securement are known, such as adhesives with the aid of interfitting pins and holes. Different housing shapes and manufacturing assemblies may naturally be used, such as making the upper portion integral with the lower portion, but with mating halves or parts.

A button 35 that is part of the trigger assembly protrudes in the axial direction from the top or distal end of housing portion 24. As used herein, distal and proximal refer to axial locations relative to an injection site when the device is oriented for use at such site, whereby, for example, proximal end of the housing refers to the housing end 27 that is closest to such injection site.

Button 35 is molded as a single piece from a suitably durable plastic material. As further shown in FIGS. 6a-6f, button 35 includes an end disc 40 with a skirt 42 extending proximally from the outer periphery of disc 40. End disc 40 has a concave face 44 upon which a force can be directly applied in a comfortable fashion by a user to selectively plunge button 35 to trigger the device.

Two flexible wall sections 46 spaced one hundred eighty degrees apart around skirt circumference are defined by vertically extending slots 48 formed at the proximal end 49 of skirt 42. A pin 50 extends radially outward from and is formed integrally with each wall section 46. Pins 50 serve as followers that fit into and can slide within tracks 52 provided in housing halves 28, 28' near housing distal end 33. Two pins 50 spaced 180 degrees apart around the button periphery are provided to balance forces and to provide a robust design, but fewer or additional pins and associated housing tracks may be provided.

Tracks 52 are shown as openings extending through housing halves 28, 28' but alternatively could be recesses formed on the inner walls of such halves. In a still alternate embodiment, rather than being directly provided on the outer housing, tracks 52 could be provided on components that are secured to housing 22. The arrangement of the tracks 52 and followers 50 on the housing halves and the button could be switched. The flexibility of wall sections 46 resulting from slots 48 aids in assembly of the button 35 with the outer housing 22.

The inner surface 57 of skirt 42 defines an interior hollow 55 in which a drive element 60 of the trigger extends. Although shown as being continuous but for the slots 48, skirt 42 need not be so configured, such as by including openings therein, while still providing an interior hollow in which the drive element may be provided.

The trigger drive element 60 is shown as a single plate-shaped member within interior hollow 55 which extends downward from disc 40 and divides the interior hollow 55 in half. Plate 60 is transversely oriented relative to the axial direction in which skirt 42 extends, and arranged diametrically within the cylindrical hollow 55. Although continuous in its transverse spanning of hollow 55 in the shown embodiment, in alternate embodiments the trigger drive element may be discontinuous, such as if it were provided as two smaller flanges, or cantilevered from one region of the inner circumference of skirt 42, or if it depended from the underside of button disc 40 in spaced relationship with skirt inner surface 57.

A biasing element 63 provides a biasing force urging button 35 upward relative to outer housing 22. Biasing element 63 is shown in FIG. 2 as a preloaded coiled spring having an upper end 64 that engages the button proximal end 49 and a lower end 65 that seats on radially protruding ribs 67 provided on the inner walls of housing halves 28, 28'. Different known types of biasing elements could alternatively be used.

Figure 7:
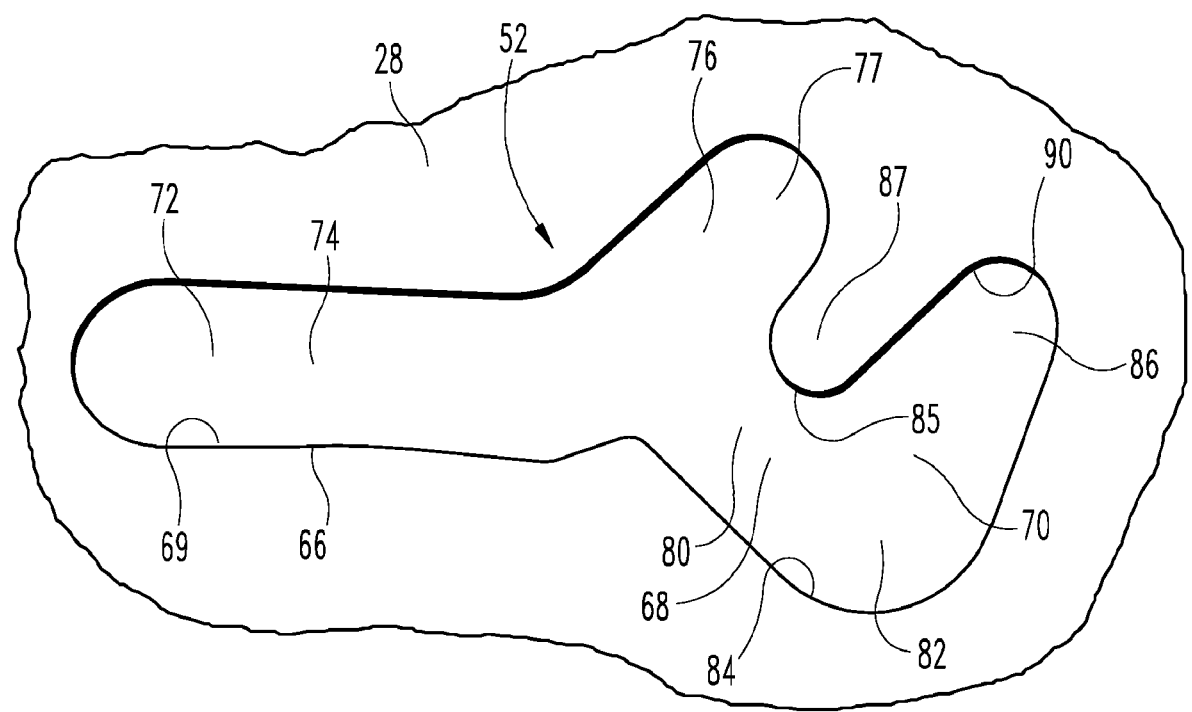
FIG. 7 is a partial view of a housing upper portion showing its button track in a two-dimensional form.
Figure 8A:
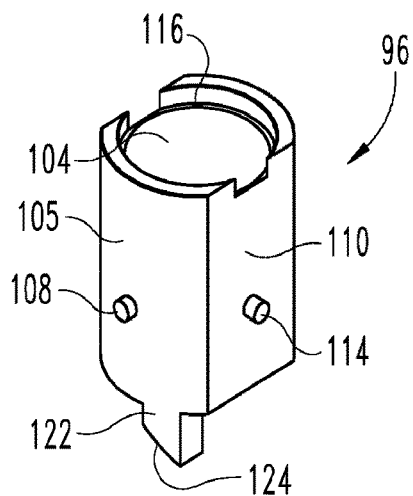
FIGS. 8a, 8b, 8c, 8d and 8e are respectively perspective, front, side, top and bottom views of one piece of a biased drive element assembly shown separate from the other device components.
Figure 8D:
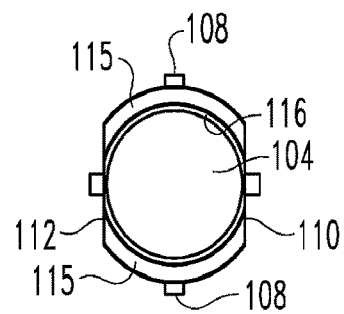
Figure 8B:
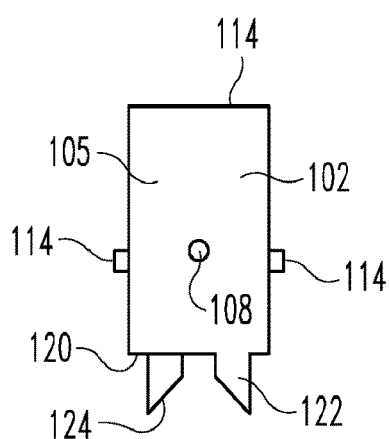
Figure 8C:
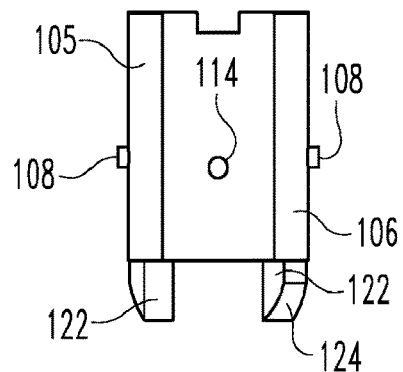
Figure 8E:
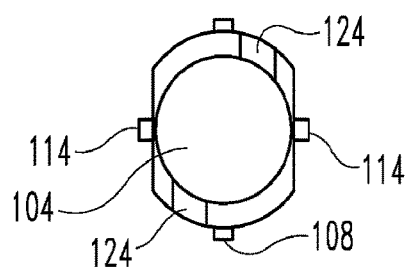
Figure 9A:
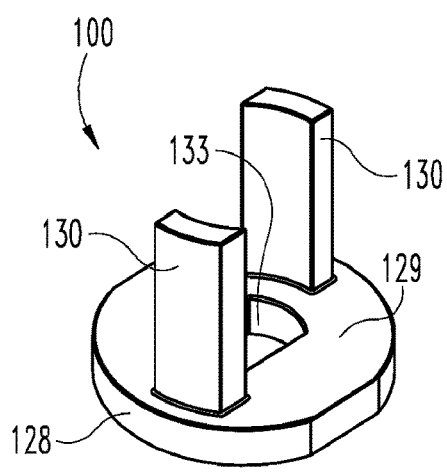
FIGS. 9a, 9b, 9c, 9d and 9e are respectively perspective, front, side, top and bottom views of a second piece of a biased drive element assembly shown separate from the other device components.
Figure 9D:
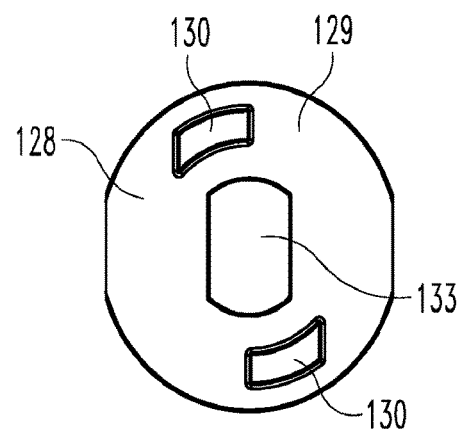
Figure 9B:
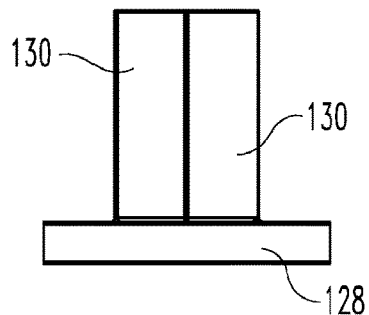
Figure 9C:
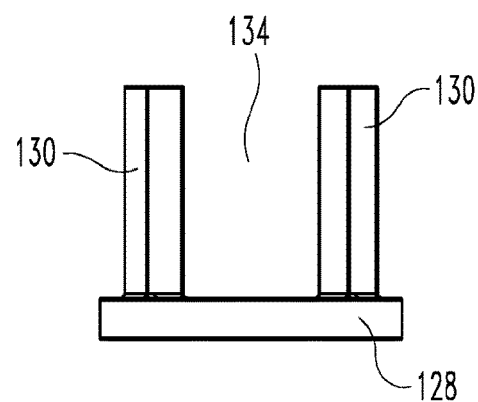
Figure 9E:
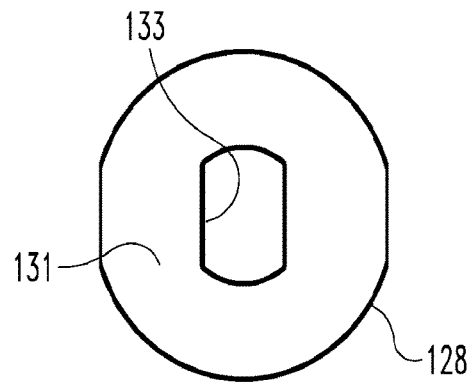
Figure 10C:
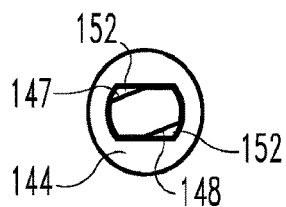
FIGS. 10a, 10b, 10c and 10d are respectively perspective, side, top and bottom views of a plunger rod shown separate from the other device components.
Figure 10A:
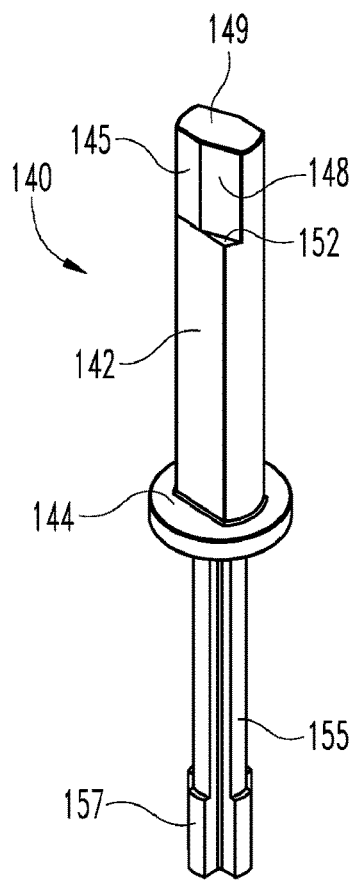
Figure 10B:
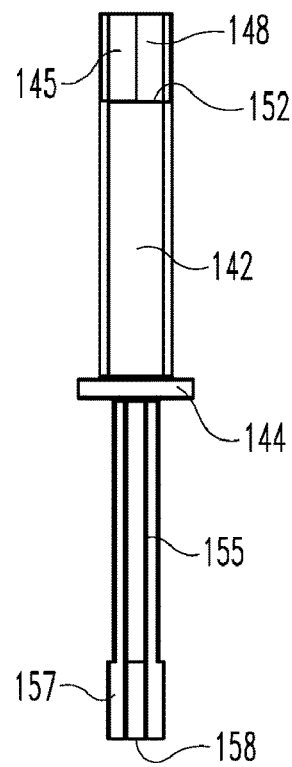
Figure 10D:
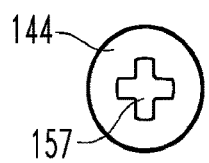

Movement of button 35 relative to housing 22 is guided by the configuration of tracks 52 in which pins 50 travel. With additional reference to FIG. 7, each track 52 defines an unlocking travel path 66, a triggering travel path 68, and a button retracting path 70. When button 35 is in a locked arrangement because pins 50 are at locked positions 72, any attempt by a user to plunge button 35 downward or into housing 22 to trigger an injection is thwarted by the abutment of pins 50 against the housing edge 69 that defines the lower extent of path 66. Unlocking travel path 66 starts at an angular end or locked position 72 and extends horizontally or circumferentially at 74 until reaching an angled upward branch 76 having an upper end 77 that serves as an unlocked or ready position The triggering travel path 68 begins at a position 80 directly below upward branch 76. Travel path 68 continues from position 80 to an axial downward and angularly offset position 82. The housing edge 84 that defines the lower extent of path 68 between positions 80 and 82 serves to cam pins 50 to thereby rotate button 35 within housing 22 as button 35 is plunged downward. Edge 84 can serve its camming function while being straight as shown or by being differently shaped, such as strictly arcuate. The upper edge 85 defining the upper extent of path 68 forms a lobe 87 that does not impact button plunging but which serves as an abutment that guides pins 50, with the assistance of biasing element 63, into upward branches 76 during device unlocking.

Button retracting path 70 continues from position 82 to an upward and angularly offset position 86. The upper edge 90 defining the upper extent of path 70 is shaped to urge a pin 50 that is pushed by the force of spring 63 upward against it to move toward position 86, thereby promoting a proper rotation of button 35.

During the triggering of device 20, the trigger drive element 60 operatively engages at least one upstanding member that extends from a drive element that is biased down by a biasing element other than spring 63. The biased drive element of device 20 is for the shown embodiment identified generally at 95 and is assembled from a first piece 96 and a second piece 100 that are fixedly secured together during manufacture. Biased drive element 95 serves as a driver of a plunger in the shown embodiment.

The foregoing as well as subsequent description of the assembly used to trigger operation of device 20 is provided for purposes of illustration and is not intended to limit a device of the present invention to such a trigger. Instead, alternate triggers, such as one or more latching prongs that are cammed out of a latching engagement by a strictly axially moving button, or others that have a known form, may be employed. The shown trigger mechanism may be further understood in view of a provisional patent application, filed with the United States Patent and Trademark Office on the same date of this application and entitled "Trigger Assembly for Automatic Medication Injection Device", the entire disclosure of which application is incorporated herein by reference.

Biased drive element piece 96 is further shown in FIGS. 8a-8f and includes an axially extending body 102 through which an axially extending, cylindrical opening or throughbore 104 is provided. Around its periphery the body 102 includes two curved body sections 105 and 106 that are each provided with a follower in the form of a pin 108. Body sections 105 and 106 are circumferentially spanned by flat body sections 110 and 112 each provided with a mounting pin 114. Pins 108 slide within tracks generally designated 109 provided in housing halves 28, 28'. Although shown as openings extending through housing halves 28, 28', tracks 109 could be differently provided, such as recesses formed on the inner walls of the housing halves, or on components that are secured to housing 22.

As further shown in FIG. 4c, each track 109 sequentially includes a horizontally aligned release region 310, an axially or vertically aligned driving region 312 that begins at one angular end 314 of release region 310, and an angled region 316 that beings at the bottom end 318 of driving region 312, and extends back in the angular direction toward release region 310 to an end 320 generally below the start end 322 of release region 310. Fewer or additional pins 108 and tracks 109 than shown may be used. At the distal end 115 of body 102, opening 104 is radially enlarged so that a substantially annular seat 116 is formed. At the proximal end 120 of body 102, each body section 105 and 106 is provided with a depending flange 122 having an angled end 124 for camming purposes described below, which angling extends in the circumferential direction.

Biased drive element piece 100 is further shown in FIGS. 9a-9f and includes a generally disc-shaped body 128 with a keyed opening 133 centrally provided therethrough. Body 128 is sized and shaped to fit in the top of body 102 so as to seat on annular seat 116, wherein it is fixedly secured such as with adhesives so that biased drive elements pieces 96 and 100 function as a single part.

Biased drive element piece 100 includes a trigger component complementarily designed with the trigger drive element 60 of button 35. This complementary design achieves a transfer of rotational motion to the biased drive element piece 100 during button plunging, and preferably does not cause the biased drive element piece 100 to move when the button, if provided with such functionality as in the shown embodiment, is rotated to be unlocked.

At least one, and in the shown embodiment a pair of, upstanding members 130 which are part of the device trigger mechanism project upward from the top surface 129 of body 128. Each upstanding member 130 is bar-shaped with a slight curving as it extends in the angular direction. Members 130 are disposed on opposite sides of body opening 133, and are in spaced relationship in the horizontal direction to provide an opening or gap 134 therebetween in which fits trigger drive element 60 when device 20 is assembled. The size and spacing of members 130 is complementarily shaped with drive element 60 so that a rotation of button 35 when plunged such that its pins 50 move from position 80 to position 82 forces a rotation of the biased drive element 95. In an alternate embodiment, and provided accommodations were made for the keyed opening 133 and its function, the upstanding members 130 could be replaced with an upstanding, off-centered flange equivalent to drive element 60, and the drive element 60 could be replaced with depending members equivalent to members 130. Still further, the upstanding members alternatively may be differently shaped.

The biased drive element 95 acts on a plunger rod, generally designated 140, when shifted proximally in the device housing from a ready position immediately prior to moving axially to a plunged position after such axial movement. As further shown in FIGS. 10a-10d, plunger rod 140 is molded to include an upper bar 142 that extends from a disc portion 144. Upper bar 142 has along the majority of its height a periphery sized and shaped to be able to closely fit within keyed opening 133. This periphery is different at the upper region 145 of upper bar 142 due to opposite corners 147 and 148 being beveled to form axially upwardly facing ledges 152. A cruciform shaped lower bar 155 sized and shaped to fit within a medication syringe depends from disc portion 144. The end region 157 of lower bar 155 is radially enlarged and includes a proximal end face 158 that operationally abuts syringe piston 167 during plunger advancement. The radial enlargement of end region 157 may help ensure the plunger rod stays secure within the syringe 160. Plunger rod 140 may be formed of two or more pieces fixedly secured together, such as with set screws, or may be formed as a single piece.

Figure 3:
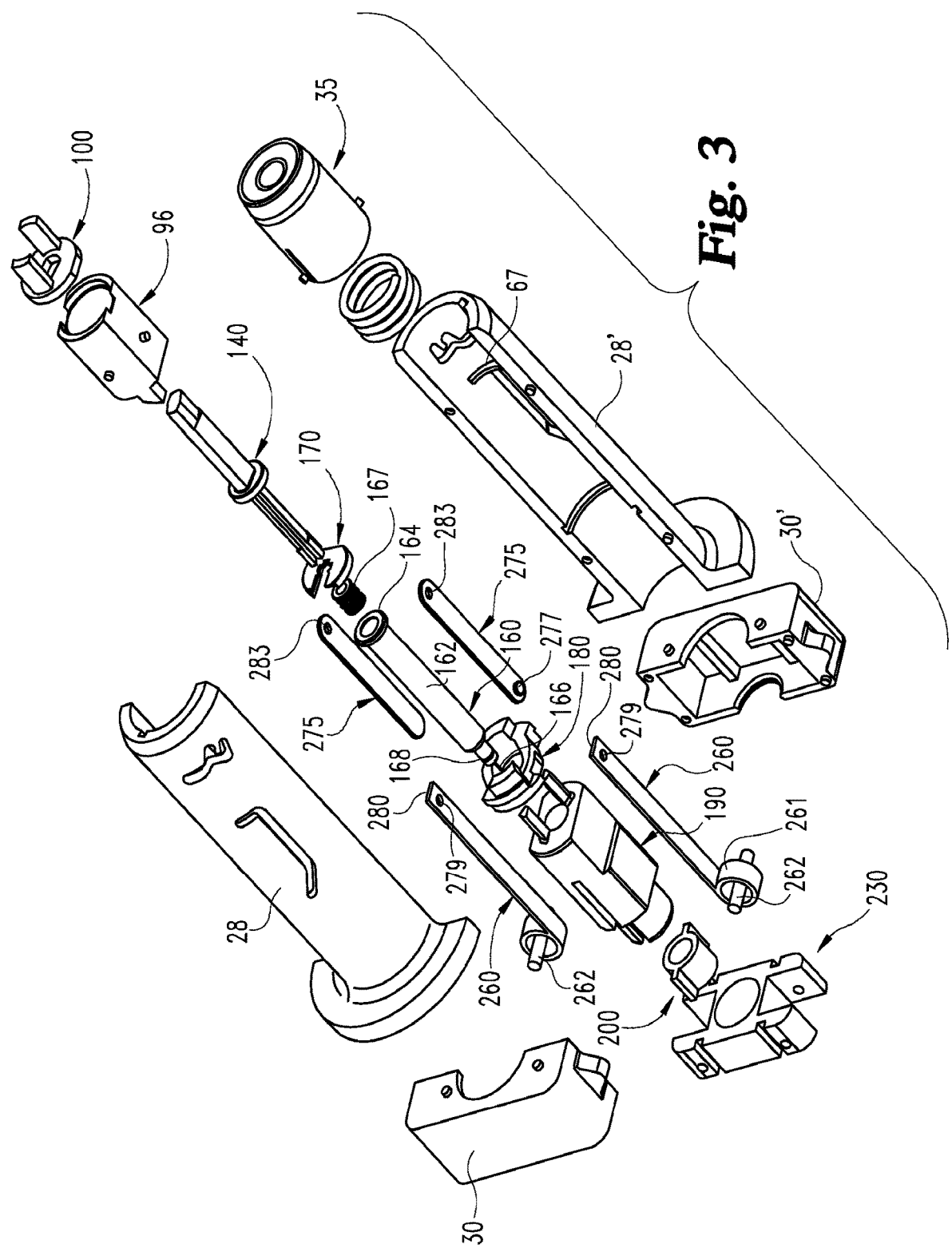
FIG. 3 is an exploded perspective view of the automatic medication injection device of FIG. 1, where the needle shield is not shown.
Figure 6A:
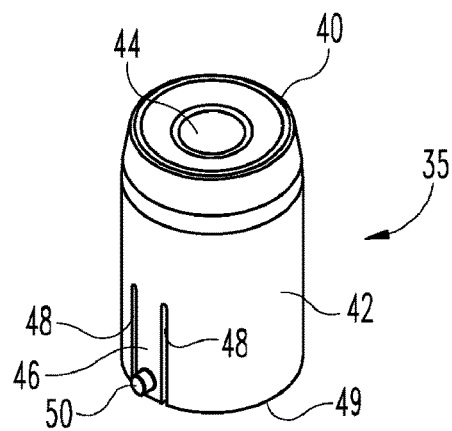
FIGS. 6a, 6b, 6c, 6d, 6e and 6f are respectively perspective, bottom perspective, front, side, top and bottom views of a button shown separate from the other device components.
Figure 6B:
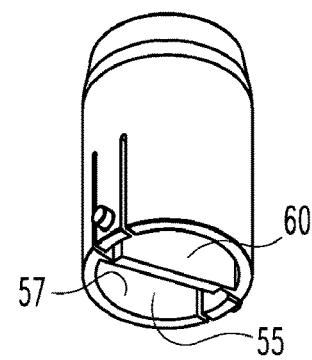
Figure 6C:
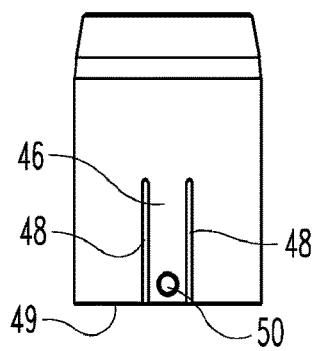
Figure 6D:
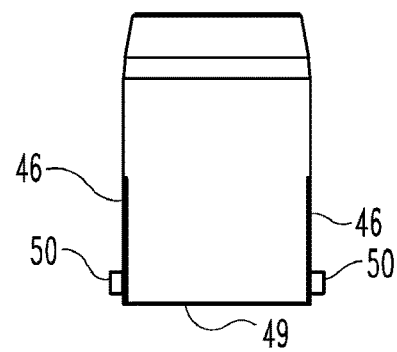
Figure 6E:
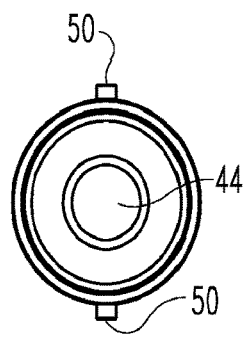
Figure 6F:
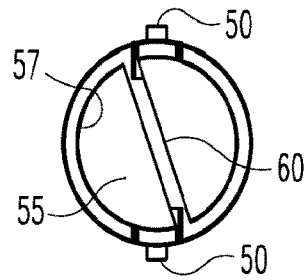

As further shown in FIG. 3, device 20 includes a medication-filled syringe of conventional design. The syringe, generally designated 160, includes a barrel 162 with a flange 164 at its distal end, and an injection needle 166 mounted at the proximal end of barrel 162 and in fluid communication with the medication contents of the barrel. Syringe piston 167 seals with the interior wall of barrel 162 and is sealingly advanceable to force the medication within the barrel out the needle 166. Syringe piston 167 and plunger rod 140 together serve in the shown embodiment as a plunger of the syringe of device 20. In an alternate embodiment, the plunger and driver of the device that work together to achieve the operational functionality may be differently formed.

Figure 11A:
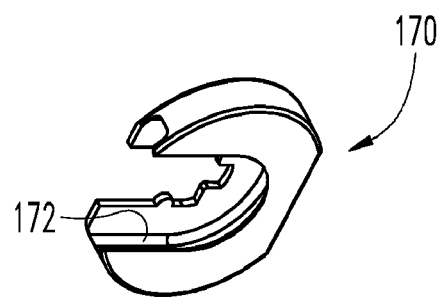
FIGS. 11a, 11b and 11c are respectively a bottom perspective, front and top views of a syringe clip shown separate from the other device components.
Figure 11C:
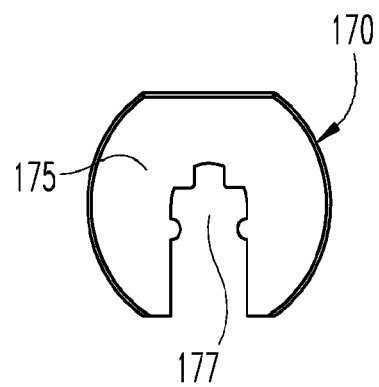
Figure 11B:
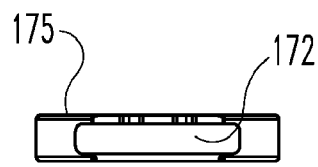
Figure 13A:
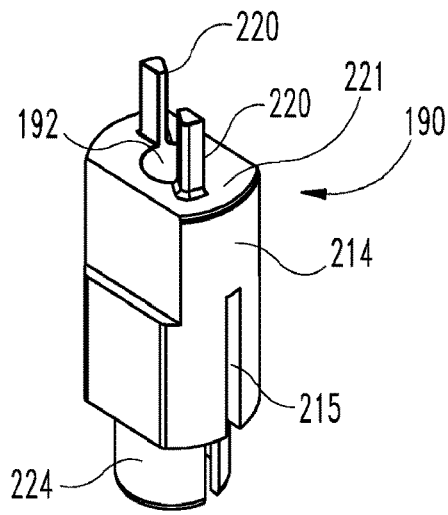
FIGS. 13a, 13b, 13c, 13d and 13e are respectively perspective, front, side, top and bottom views of an upper spring retainer shown separate from the other device components.
Figure 13B:
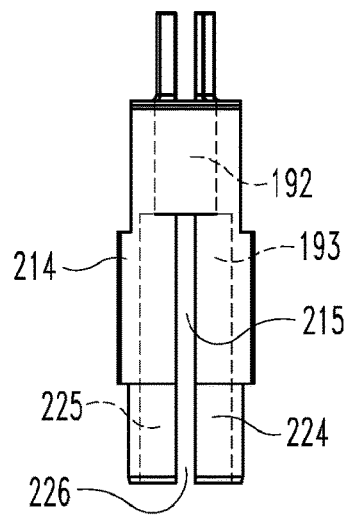
Figure 13C:
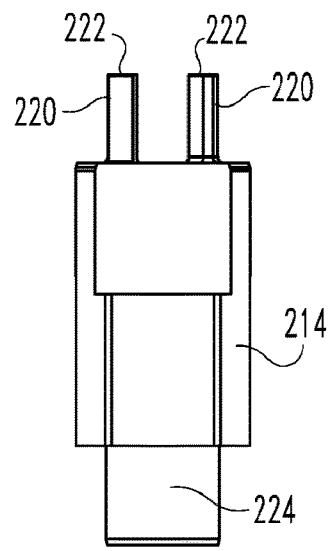
Figure 13D:
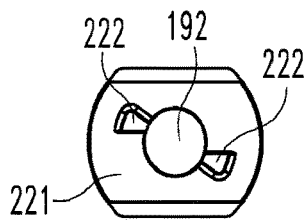
Figure 13E:
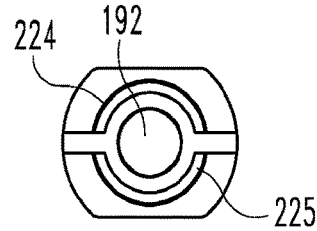
Figure 14A:
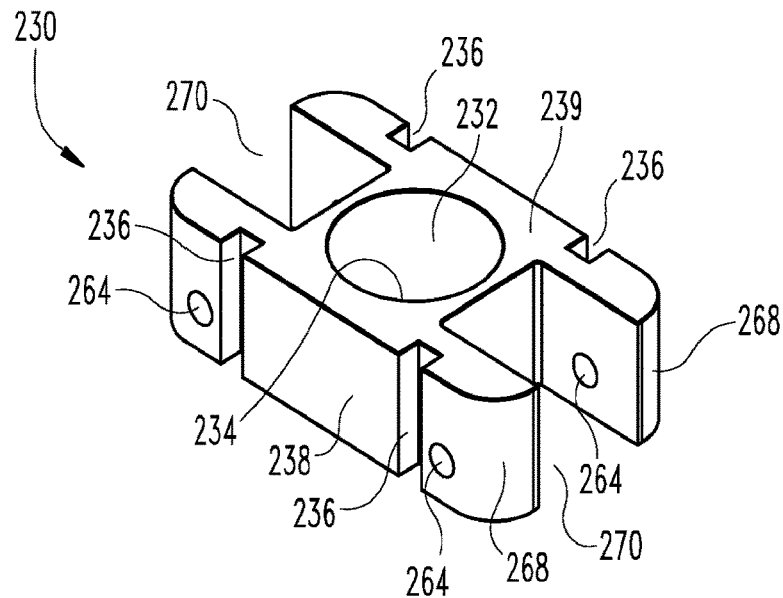
FIGS. 14a, 14b, 14c and 14d are respectively perspective, front, side and top, as well as bottom, views of a lower spring retainer shown separate from the other device components.
Figure 14B:
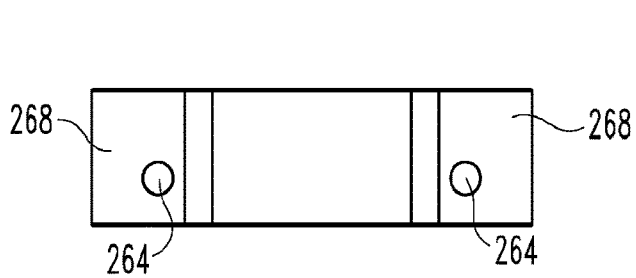
Figure 14C:
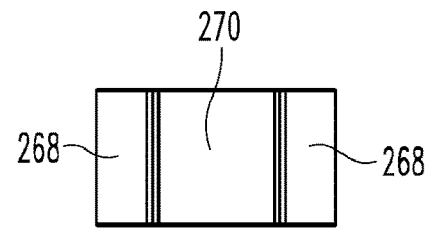
Figure 14D:
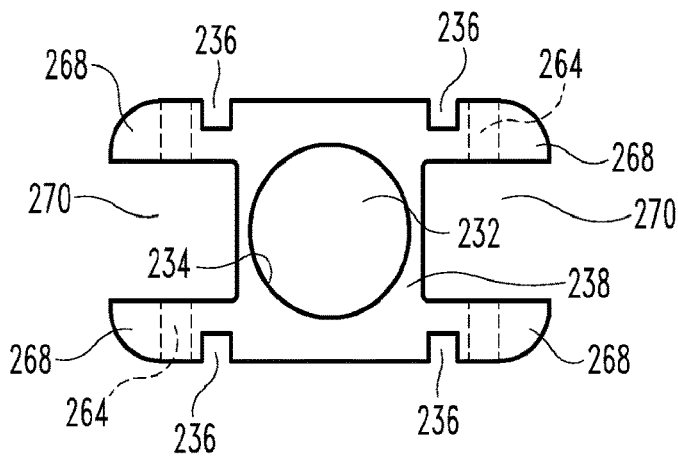
Figure 15A:
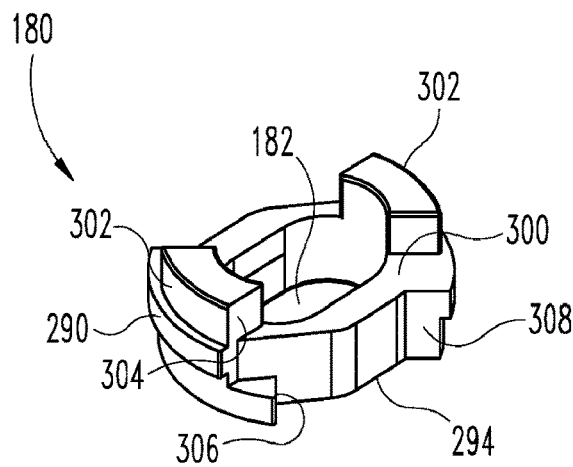
FIGS. 15a, 15b, 15c, 15d, 15e and 15f are respectively perspective, front, side, top, bottom and bottom perspective views of a retraction plate shown separate from the other device components.
Figure 15B:
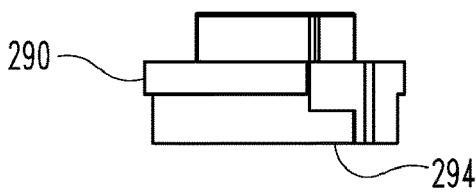
Figure 15C:
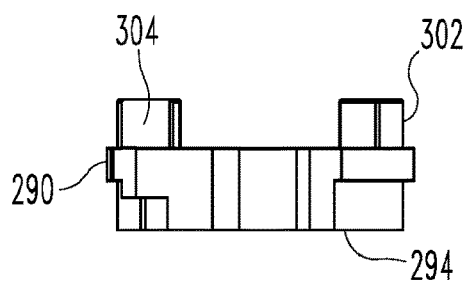
Figure 15D:
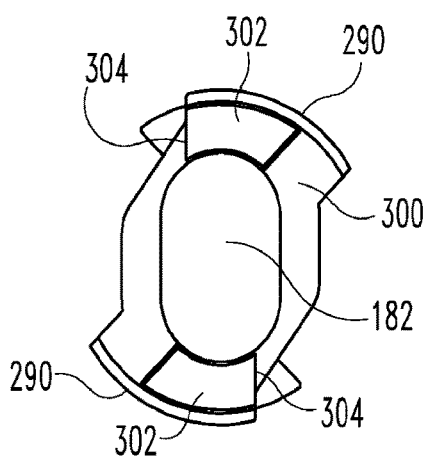
Figure 15E:
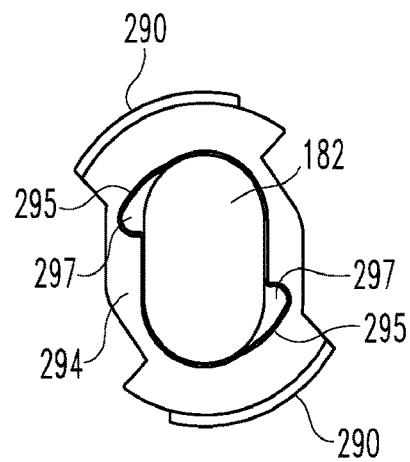
Figure 15F:
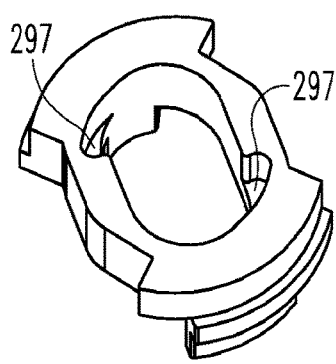

A syringe clip 170 further shown in FIGS. 11a-11c includes a transversely opening, syringe flange-accommodating hollow 172 and mounts to syringe barrel flange 164 to be rotatably fixed together. The syringe clip 170 can frictionally lock to flange 164, possibly with the aid of an inner lining having a high coefficient of friction, or can with a modification in the syringe flange and clip design have a keyed together fit. The top wall 175 of clip 170 includes a keyed opening 177 which matches the size and shape of and receives plunger rod bar 155 to limit the rotation of plunger rod 140 relative to syringe barrel 162. Syringe clip 170 aids in locating the syringe 160 within the interior of the device housing.

In an alternate embodiment, the lower bar 155 may have a different shape than the cross shape shown, for example a D-shape cross-section, that fits with a corresponding keyed opening in a modified syringe clip 170. Also, the syringe clip could be still differently shaped than as described above, such as a plate that is fixedly secured to the syringe flange, such as with set screws, and without a transversely opening hollow for the flange.

Syringe barrel 162 freely extends through an opening or throughhole 182 in retraction plate 180 and an opening or throughbore 192 in an upper spring retainer 190. The proximal region of barrel 162 fits within an opening or bore 202 through a body 204 of syringe guide 200, which guide is further shown in FIGS. 12a-12e. Body 204 is generally annular and extends from a distal face 208 to a proximal face 207. Bore 202 has a reduced diameter portion 203 at its proximal end which allows passage therethrough of the needle 166 and reduced diameter needle-holding end 168 of the syringe barrel. The region of body 204 that defines bore portion 203 provides an annular collar 206 shaped to correspond to the barrel neck and to prevent passage of the syringe barrel 162 entirely through the syringe guide 200. Guide body 204 is sized to have a frictional fit with barrel 162 that resists rotational motion of the syringe 160 within syringe guide 200.

Each of throughhole 182, throughbore 192, bore 202 and bore 232 are circumscribed by the bodies of the elements in which they are provided in the shown embodiment. In alternate embodiments, one or more such hole or bores may be not so completely ringed or circumscribed so long as the functionality of such element is not compromised. Throughhole 182, throughbore 192, bore 202 and bore 232 are all coaxially aligned with keyed opening 133 as well as the longitudinal axis of syringe 160.

Syringe guide 200 is rotatably fixed and axially shiftable relative to an upper spring retainer 190 that is further shown in FIGS. 13a-13e. This relationship is provided by flange-shape keys 210 of syringe guide 200 which are slidable within axially extending slots 215 in body 214 of upper spring retainer 190 when guide 200 shifts within a radially enlarged portion 193 of throughbore 192. Syringe guide 200 may provide a frictional fit with retainer 190 to hold the syringe 160 in a retracted position.

In an alternate embodiment not shown, syringe 160 can be held in a retracted position by the combination of syringe clip 170 seating on the upper extent of end region 157, and the plunger rod 140 releasably catching on biased drive element piece 100, such as via one or more pins at the top end of plunger rod 140 that engage top surface 129 until such pins are aligned to fit through opening 133 after biased drive element piece 100 is rotated during triggering.

Two spacing fingers 220 project upward in the axial direction from the upper face 221 of body 214. The distal faces 222 of fingers 220 engage retracting plate 180 as described below. Fingers 220 are disposed on diametrically opposed sides of throughbore 192.

An annular assembly collar 224 depends from the proximal end of body 214. The hollow interior 225 of collar 224 allows for the injection needle 166 to extend therethrough. Slots 226 aligned with slots 215 allow for insertion of syringe guide 200 into body 214 during device assembly. Collar 224 fits within a central, cylindrical bore or aperture 232 axially extending through lower spring retainer 230. Collar 224 is fixedly secured within bore 232, such as by adhesively attaching, and/or attaching using screws or other fasteners, collar 224 to retainer surface 234.

As further shown in FIGS. 14a-14d, lower spring retainer 230 includes grooves or keyways 236 on opposite sides of its body 238. Keyways 236 fit over vertically extending ribs or keys 240 in the interior hollow 242 of each of shell halves 30, 30' of housing lower portion 26, and lower spring retainer 230 is sized to be slideable in the axial direction within hollow 242. With reference to shell half 30' shown in FIGS. 5a-5f, each of shell halves 30 and 30' include a semi-circular notch 245 in an upper wall 246 and a semi-circular notch 248 in a lower wall 249. In the assembled device 20, the notches 245 define a circular opening sized and shaped to freely receive spring retainer body 214 and biasing springs described further below, while notches 248 define a smaller circular opening sized to merely allow passage of the needle 166 and fitting of the needle shield 29 over needle 166 before device use.

In the shown embodiment, lower spring retainer 230 and upper spring retainer 190 serve with syringe guide 200 as a retractor of the syringe after an injection. The retractor is shiftable distally to withdraw the syringe from an injection position to a retracted position at which the syringe needle is disposed within the housing.

Lower spring retainer 230 is connected to the proximal end of biasing springs used to power the medication delivery by device 20. Biasing springs of device 20 are shown in FIG. 3 as a pair of constant force springs 260 made of a thin slat of metal that have their proximal ends wound at 261 around pins 262. The ends of pins 262 fit within transverse bores 264 formed in facing body arms 268. Each pin 262 spans, with its wound spring portion 261 fitting within, a notch 270 in body 238 that defines facing body arms 268.

Springs 260 are connected with the biased drive element that drives the syringe motion by extenders 275 that are made of metal or other suitably robust material. A boss 277 provided near the proximal end of each extender 275 snap fits within a hole 279 provided near the distal end 280 of a spring 260. Each extender 275 also includes a hole 283 near its distal end that receives a pin 114 of biased drive element piece 95. Extenders 275 facilitate biased drive element 95 turning relative to the springs 260 during device operation. Springs 260 alternatively may be connected directly to pins 114 using holes 279.

Spring 260 are shown as two in number disposed on opposite sides of the spring retainer formed by the assembly of upper spring retainer 190 and lower spring retainer 230. Such a spring configuration provides a balancing of forces within the device, but fewer or additional springs could be employed. Each spring 260 is preloaded and shown to have constant force properties to cause a constant force to be provided to shift the syringe downward so as to insert the needle 166 into a user, a constant force to be provided to force the medication contents of the syringe 160 through the needle 166, and a constant force to retract the needle 166 into the housing 22 after dose delivery. In addition, in an alternate embodiment, such as by having different sections of the springs 260 having different widths, springs 260 can provide one constant force during one phase of operation and a different constant force during another phase of operation. Springs that do not provide constant force during one or more or all phases of device operation may alternatively be employed.

In alternate embodiments, one or more additional springs, as well as possibly different configurations of springs 260, may be employed to provide benefit to device operation. For example, one or more additional springs may be interposed, in a preloaded state, between the bottom surface of lower spring retainer 230 and the lower wall 249 of shell halves 30, 30' of housing lower portion 26, which interposed springs provide a force to assist springs 260 in retracting the syringe needle within the housing after an injection. Furthermore, such interposed springs could provide the sole syringe retraction force, such as if springs 260, at their lower ends, were not operatively attached to the lower spring retainer but instead were attached directly to the housing, such as interior walls of housing lower portion 26 if lower spring retainer 230 were made smaller to allow such spring positioning.

A retraction plate 180 further shown in FIGS. 15a-15f is used to stage needle retraction by serving as a blocking member. Ribs or keys 290 that protrude radially outward fit within horizontal grooves 292 in housing shell halves 28, 28' and slide therein so that retraction plate 180 is axially captured but rotatably shiftable within outer housing 22. The underside 294 of plate 180 includes two notches 295 that open to the oblong throughhole 182 and provide two axially facing stop surfaces 297. When retraction plate 180 is in a blocking rotational position within housing 22 associated with device 20 being in a pre-injection arrangement, the spacing fingers 220 of upper spring retainer 190 project within notches 295 so that finger distal faces 222 abut stop surfaces 297. When retraction plate 180 is in a second rotational position within housing 22 for needle retraction, fingers 220 project within throughhole 182 to be freely insertable therethrough.

The top surface 300 of retraction plate 180 includes two bosses 302 on opposite sides of throughhole 182. Each boss 302 has an angular end 304 that serves as a push surface during the forced rotation of the retraction plate 180. The cut out that creates surfaces 306 and 308 serves as an opening through which springs 260 axially extend, as well as reduces points of contact with the housing, which contacts points would otherwise create additional frictional resistance to rotation.

Retraction plate 180 could also be modified in a not shown alternate embodiment to provide a more robust design that also serves a guiding function. For example, the periphery of plate 180, at opposite regions of its circumference, could include downwardly depending flanges. These flanges would generally flank upper spring retainer 190 and guide that retainer 190 as it moves upward to have fingers 220 insert within throughhole 182 as described below. The flanges may be designed to assist fingers 220 by engaging upper spring retainer 190 to prevent the retainer 190 from moving upward when the retraction plate 180 is in a first or starting rotational position within the housing, and by being free of the retainer 190 to allow upward motion of retainer 190 into the space between the flanges when the retraction plate 180 reaches its second rotational position. In addition, in this alternate embodiment the bottom ends of the downwardly depending flanges could serve as stops against which shoulders of the upper spring retainer 190 abut to halt the syringe retraction after use at a desired height.

The construction of device 20 will be further understood in view of a description of its operation. A user starts with a device 20 configured in a locked state as supplied by the manufacturer and as shown in FIG. 1.

A user first pulls the needle shield 29 off the device. The needle 166 of syringe 160 does not extend at this point beyond the base of housing lower portion 26 and is still protectively housed within housing 22.

To unlock the device 20 for injection, button 35 is manually rotated relative to housing 22 such that pins 50 slide along travel paths 66 until reaching ends 77. Spring 63 urges the button 35 upward to encourage the pins 50 to travel toward ends 77. During this button rotation, neither the biased drive element 95 nor any of the other internal components are moving, and notably trigger drive element 60 spins within gap 134 without movably contacting upstanding members 130. At this point the device 20 is arranged as shown in FIG. 2.

To begin an injection when device 20 is properly positioned on an injection site, when a user subsequently applies a manual plunging force on face 44 of button 35 sufficient to overcome spring 63, button 35 first moves downward and pins 50 slide past lobe 87 and reach position 80. Further button plunging by the user from that point causes button 35 to rotate as pins 50 slide along the angled housing edge 84 until reaching the position 82. The button rotation within housing 22 resulting from pins 50 moving from position 80 to position 82 forces biased drive element 95 to turn within housing 22 due to trigger drive element 60 drivingly contacting members 130. During this turning of biased drive element 95, pins 108 slide within track release regions 310 until reaching ends 314. This rotation of biased drive element 95 does not move plunger rod 140, despite the distal end 149 being at this point disposed at an elevation above or within the keyed opening 133 of biased drive element body 128. Rather, during this rotation, the biased drive element 95 moves such that portions of the surface that forms its keyed opening 133 end up adjacent to the surfaces of beveled corners 147, 148. Removal of a plunging force on button 35 at any time after pins 50 reach position 82 results in the button 35 being urged up by spring 63 to cause the button to move up and rotate till pins 50 reach position 86.

When pins 108 reach track end 314 in alignment with track driving region 312, biased drive element 95 is driven or pulled downward, with pins 108 traveling down track driving region 312, due to a downward pulling force of constant strength on biased drive element 95 resulting from a preloading of springs 260 during manufacturing assembly. The assembly of lower spring retainer 230 and upper spring retainer 190 is not pulled up within the housing 22 at this time by this spring preloading due to the abutment of fingers 220 with retraction plate 180.

As biased drive element 95 moves downward, keyed opening 133 first moves down around plunger upper region 145 without moving plunger rod 140. When biased drive element 95 moves down sufficiently, the underside 131 of body 128 abuts ledges 152, and continued downward motion of biased drive element 95 powered by springs 260 drives plunger rod 140 down. This downward driving of plunger rod 140 pushes the syringe piston 167 proximally, which motion first shifts syringe barrel 162 proximally relative to the outer housing 22, with guide 200 sliding within slots 215. Motion of syringe barrel 162 proximally is halted when guide keys 210 abut top surface 239 of lower spring retainer 230, at which point the tip of needle 166 projects beyond the housing proximal end 27 for penetrating a user's skin. Continued downward driving of plunger rod 140 by biased drive element 95 powered by springs 260 pushes syringe piston 167 to slide within the syringe barrel 162 to force the medication contents of the syringe through that needle 166 for an injection.

Throughout the needle insertion and the start of the medication injection process described above, pins 108 are traveling down track driving region 312 with biased drive element 95 translating without rotation within housing 22. When pins 108 reach end 318 of track driving region 312, the medication contents are not yet completely delivered, and pins 108 continue into and slide downward within angled region 316 of track 109. Biased drive element 95 translates as well as rotates within housing 22 when pins 108 slide along angled region 316. Due to the keying of plunger rod 140 to syringe clip 170, and the amount of resistance to rotation provided between syringe clip 170 and syringe 160 as well as between syringe 160 and syringe guide 200, as biased drive element 95 so rotates, the underside 131 of body 128 begins to spin on the ledges 152 as it continues to drive the plunger rod 140 proximally. When biased drive element 95 has rotated sufficiently, which point is designed to correspond to when the syringe piston 167 has forced a proper dose from the syringe 160 and pins 108 have reached end 320 of angled region 316 so that movement of biased drive element 95 is stopped, keyed opening 133 clears ledges 152. This ledge clearance will allow retraction of the plunger rod 140.

When biased drive element 95 so rotates within housing 22 when pins 108 slide along angled region 316 as described above, it has a camming, driving relationship with retraction plate 180. The angled ends 124 of flanges 122 contact angular ends 304 of bosses 302, and the rotation of biased drive element 95 drives the rotation of retraction plate 180 within housing 22. When pins 108 reach ends 320 of track angled regions 316, retraction plate 180 reaches a point of sufficient rotation at which stop surfaces 297 are angularly clear of finger distal faces 222, thereby allowing fingers 220 to insert within retraction plate opening 182. The clearance of ledges 152 by keyed opening 133 is designed to be simultaneous with retraction plate surfaces 297 being clear from finger distal faces 222. FIG. 16 shows device 20 arranged at this point of operation.

When fingers 220 are aligned to insert within opening 182, springs 260 pull the assembly of lower spring retainer 230 and upper spring retainer 190 upward within housing 22 until top surface 239 of lower spring retainer 230 abuts the inside of the upper wall 246 of housing lower portion 26. Because syringe guide keys 210 are abutting surface 239, the upward pulling of the assembly of lower spring retainer 230 and upper spring retainer 190 lifts the syringe 160 within housing 22 to retract the tip of needle 166 into a protectively housed position within housing 22. As the syringe 160 is being so retracted, plunger rod 142 extends further upward through keyed opening 133. At this point, device 20 has completed its operation and is arranged as shown in FIG. 17.

While this invention has been shown and described as multiple possible designs, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

We claim:

1. An automatic medication injection device comprising:
   a housing;
   a syringe filled with medication and including a needle and a plunger;
   a driver shiftable proximally in said housing along a track from a ready position to a plunged position, said driver and said track and said plunger being complementarily configured for said driver, when shifted from said ready position to said plunged position, to advance said plunger to move said syringe proximally from a start position, at which said needle is disposed within said housing, to an injecting position, at which said needle projects external to said housing, and to advance the plunger to expel medication from the syringe through said needle, and to disengage from said plunger to permit axial movement of said driver relative to said plunger;
   a retractor having an opening in which said syringe extends, said retractor shiftable distally within said housing from a ready position to a retraction position to withdraw said syringe from said injecting position to a retracted position at which said needle is disposed within said housing;
   a blocking member having an opening in which said syringe extends, and disposed distal to the retractor along the syringe, said blocking member rotatable within said housing from a first rotational orientation to a second rotational orientation, said blocking member complementarily configured with said retractor to block movement of said retractor from said ready position to said retraction position when disposed in said first rotational orientation, and to permit movement of said retractor from said ready position to said retraction position when disposed in said second rotational orientation;
   at least one biasing member preloaded to urge said driver proximally and to urge said retractor distally;
   a trigger actuatable to allow said at least one biasing member to move said driver from said ready position to said plunged position; and
   said driver and said blocking member having a complementary camming configuration for said blocking member to be forcibly rotated automatically from said first rotational orientation to said second rotational orientation when said driver shifts from said ready position to said plunged position.

2. The automatic medication injection device of claim 1 wherein said blocking member comprises a body including one of a key and a groove, and an interior surface of said housing comprises the other of said key and said groove, said key sliding within said groove when said blocking member rotates from said first rotational orientation to said second rotational orientation.

3. The automatic medication injection device of claim 1 wherein said blocking member comprises a body, and said opening in said blocking member is circumscribed by said body.

4. The automatic medication injection device of claim 1 wherein said retractor comprises a body, and said opening in said retractor is circumscribed by said body.

5. The automatic medication injection device of claim 1 wherein said retractor includes at least one finger that projects from a distally facing surface of a body of said retractor and which terminates in a distal end, and wherein a body of said blocking member includes at least one notching on an underside surface, said at least one notching extending from said opening in said blocking member, wherein said distal end of said at least one finger fits within said at least one notching when said blocking member is in said first rotational orientation and engages said body of said blocking member so that said retractor is blocked from moving from said ready position to said retraction position, said at least one finger fitting within said opening in said blocking member when said blocking member is in said second rotational orientation.

6. The automatic medication injection device of claim 5 wherein said at least one finger includes two fingers that are disposed on opposite sides of said opening in said retractor and extend in an axial direction.

7. The automatic medication injection device of claim 1 wherein said at least one biasing member comprises a constant force spring.

8. The automatic medication injection device of claim 1 wherein said at least one biasing member has opposite ends operatively attached to said driver and said retractor.

9. The automatic medication injection device of claim 8 wherein said at least one biasing member comprises a constant force spring having a winding that encircles a pin mounted to said retractor.

10. The automatic medication injection device of claim 1 wherein said a least one biasing member comprises a pair of constant force springs axially extending along opposite sides of said retractor.

11. The automatic medication injection device of claim 1 wherein said track comprises an axially extending slot that opens to an angled slot, both said axially extending slot and said angled slot being provided on said housing, and wherein said driver includes a follower that slides within said axially extending slot and said angled slot.

12. The automatic medication injection device of claim 1 wherein said driver includes a keyed opening for engaging said plunger, and wherein said keyed opening and said retractor opening and said blocking member opening are coaxially aligned with said syringe.

13. The automatic medication injection device of claim 1 wherein said driver includes a keyed opening for said plunger, and said plunger includes a ledge on which said driver applies a plunging force, said driver rotatable relative to said plunger to disengage from said ledge to permit said plunger to move axially through said keyed opening.

14. The automatic medication injection device of claim 1 further comprising a syringe guide in which non-rotatably fits said syringe, said syringe guide keyed with said retractor to permit limited relative axial movement and to prevent relative rotational motion, said retractor driving said syringe guide distally to withdraw said syringe from said injecting position to said retracted position.

15. The automatic medication injection device of claim 1, wherein the retractor further comprises at least one retainer disposed proximal to the blocking member, the at least one retainer being axially shiftable relative to the blocking member.

16. The automatic medication injection device of claim 15, wherein the at least one retainer comprises an upper retainer and a lower retainer disposed proximal to the upper spring retainer, and said blocking member is complementarily configured with the upper retainer to block movement of said retractor from said ready position to said retraction position when disposed in said first rotational orientation, and to permit movement of said retractor from said ready position to said retraction position when disposed in said second rotational orientation.

17. The automatic medication injection device of claim 16, wherein the lower retainer is coupled to the housing and axially shiftable relative to the housing.

18. An automatic medication injection device comprising:
a housing;
a syringe configured to contain a medication, and the syringe including a needle and a plunger;
an axially shiftable driver proximally movable from a ready position to a plunged position in said housing, when shifted from said ready position to said plunged position, the driver is configured to advance said syringe proximally from a start position, at which said needle is disposed within said housing, to an injecting position, at which said needle projects external to said housing, and to advance the plunger within the syringe;
a retraction plate having an opening in which said syringe extends, said retraction plate rotatable within said housing from a first rotational orientation to a second rotational orientation,
a retraction assembly shiftable distally within said housing to withdraw said syringe from said injecting position to a retracted position at which said needle is disposed within said housing, the retraction assembly having a first component disposed proximal to the retraction plate, and shiftable distally from a ready proximal position to a retraction distal position, the first component being complementarily configured with said retraction plate to block distal movement of said first component from said ready proximal position to said retraction distal position when the retraction plate is disposed in said first rotational orientation, and to permit distal movement of said first component from said ready proximal position to said retraction distal position when said retraction plate is disposed in said second rotational orientation.

19. The device of claim 18, wherein the first component comprises at least one distal projection, and the retraction plate comprises at least one notch defining an axial stop surface in engagement with the at least one projection when the retraction plate is disposed in said first rotational orientation, wherein in response to rotation of the retraction plate from the first rotational orientation to the second rotational orientation, the at least one distal projection is cleared from the axial stop surface and is inserted within the opening of the retraction plate.

20. The device of claim 19, wherein the retraction assembly further comprises a second component disposed proximal to the first component, a guide member rotatably fixed and axially shiftable relative to the first component and disposed between the first and second components, the guide member defining an opening sized to receive a portion of the syringe, wherein in response to rotation of the retraction plate from the first rotational orientation to the second rotational orientation, the first component, the second component, and the guide member are distally shifted relative to said housing.

* * * * *

UNITED STATES PATENT AND TRADEMARK OFFICE
CERTIFICATE OF CORRECTION

PATENT NO. : 10,864,326 B2
APPLICATION NO. : 16/079414
DATED : December 15, 2020
INVENTOR(S) : Nicole Taylor Gonzalez et al.

Page 1 of 1

It is certified that error appears in the above-identified patent and that said Letters Patent is hereby corrected as shown below:

On the Title Page

On page 2, Column 1 item (73) (Abstract), Line 1, delete "syringe0," and insert -- syringe, --, therefor.

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*